United States Patent [19]
Deegan et al.

[11] Patent Number: 5,989,533
[45] Date of Patent: Nov. 23, 1999

[54] HAIR CONDITIONING COMPOSITIONS CONTAINING ALPHA OR BETA HYDROXY ACID ESTERS

[75] Inventors: Charlene Patricia Deegan, Lakehurst, N.J.; Geoffrey Robert Hawkins, Langhorne, Pa.

[73] Assignee: Revlon Consumer Products Corporation, New York, N.Y.

[21] Appl. No.: 08/897,955

[22] Filed: Jul. 21, 1997

[51] Int. Cl.⁶ .................................................. A61K 7/06
[52] U.S. Cl. ................. 424/70.28; 424/401; 424/78.03; 424/70.1; 424/70.11; 424/70.12; 514/880
[58] Field of Search ............................... 424/401, 78.03, 424/70.1, 70.11, 70.12, 70.28; 514/880

[56] References Cited

U.S. PATENT DOCUMENTS

| | | | |
|---|---|---|---|
| Re. 34,958 | 5/1995 | Garbe | 424/70.12 |
| 4,269,824 | 5/1981 | Villamarin | 424/70 |
| 4,374,825 | 2/1983 | Bolich | 424/70 |
| 4,387,090 | 6/1983 | Bolich | 424/70 |
| 4,472,375 | 9/1984 | Bolich | 424/70 |
| 4,636,329 | 1/1987 | Steuri | 252/106 |
| 4,673,568 | 6/1987 | Grollier | 424/47 |
| 4,711,776 | 12/1987 | Suzuki | 424/70 |
| 4,719,930 | 1/1988 | Gross | 132/7 |
| 4,726,945 | 2/1988 | Patel | 424/70 |
| 4,741,855 | 5/1988 | Grote | 252/142 |
| 4,752,467 | 6/1988 | Konrad | 424/70 |
| 4,765,975 | 8/1988 | Iovanni | 424/70 |
| 4,780,310 | 10/1988 | Lang | 424/47 |
| 4,797,273 | 1/1989 | Linn et al. | 424/59 |
| 4,818,523 | 4/1989 | Clarke | 424/70 |
| 4,844,888 | 7/1989 | Zawadzki | 429/69 |
| 4,855,130 | 8/1989 | Konrad | 424/70 |
| 4,886,660 | 12/1989 | Patel | 424/70 |
| 4,902,499 | 2/1990 | Bolish | 424/70 |
| 4,950,468 | 8/1990 | Nakamura | 424/70 |
| 4,954,335 | 9/1990 | Janchipraponvej | 424/70 |
| 4,975,274 | 12/1990 | Iannucci | 424/70 |
| 4,976,956 | 12/1990 | Noe | 424/70 |
| 4,988,506 | 1/1991 | Mitra | 424/81 |
| 5,002,761 | 3/1991 | Mueller | 424/70 |
| 5,021,477 | 6/1991 | Garbe | 424/70 |
| 5,061,481 | 10/1991 | Suzuki | 424/63 |
| 5,091,171 | 2/1992 | Yu | 424/642 |
| 5,100,657 | 3/1992 | Ansher-Jackson | 424/70 |
| 5,106,609 | 4/1992 | Bolich | 424/70 |
| 5,108,751 | 4/1992 | Hagan | 424/401 |
| 5,166,276 | 11/1992 | Hayama | 525/329.7 |
| 5,169,623 | 12/1992 | Kopolow | 424/47 |
| 5,213,793 | 5/1993 | Moses | 424/70 |
| 5,254,336 | 10/1993 | Hoshowski | 424/70 |
| 5,286,476 | 2/1994 | Nanba | 424/47 |
| 5,326,483 | 7/1994 | Halloran | 252/174.15 |
| 5,328,685 | 7/1994 | Janchitraponvej | 424/71 |
| 5,425,937 | 6/1995 | Uchiwa | 424/70.14 |
| 5,439,677 | 8/1995 | Villamarin | 424/70.14 |
| 5,470,551 | 11/1995 | Dubief | 424/70.12 |
| 5,480,634 | 1/1996 | Hayama | 424/70.12 |
| 5,534,265 | 7/1996 | Fowler et al. | 424/489 |
| 5,567,428 | 10/1996 | Hughes | 424/401 |
| 5,759,558 | 6/1998 | Epstein et al. | 424/401 |

FOREIGN PATENT DOCUMENTS

| | | | |
|---|---|---|---|
| 662315 | 7/1995 | European Pat. Off. | |
| 410067647 | 3/1998 | Japan | A61K 7/48 |
| 9531173 | 11/1995 | WIPO | |

OTHER PUBLICATIONS

Alzo Technical Bulletin #227 Apr. 1996.

*Primary Examiner*—Thurman K. Page
*Assistant Examiner*—Brian K. Seidleck
*Attorney, Agent, or Firm*—Julie Blackburn

[57] ABSTRACT

A hair conditioner composition comprising, by weight of the total composition:

0.1–20% of a cationic conditioning agent, 0.1–20% of esters of alpha or beta hydroxy acids, 0.1–30% of a fatty alcohol, 0.001–10% of a nonionic surfactant, and 5–95% water.

11 Claims, No Drawings

HAIR CONDITIONING COMPOSITIONS CONTAINING ALPHA OR BETA HYDROXY ACID ESTERS

TECHNICAL FIELD

The invention is in the field of hair conditioning compositions.

BACKGROUND OF THE INVENTION

Damage to hair can result from exposure to excessive heat or cold, such as with blow-drying, and exposure to sun or wind. Chemical treatments such as perming or coloring the hair also may cause hair to become weakened or damaged. Marketers of personal care products have commercialized many varieties of after-shampoo conditioners that contain ingredients which exert a conditioning effect on the hair. Unfortunately, the ingredients which condition hair also provide certain undesireable effects. Solid, nonvolatile ingredients such as fatty alcohols, resins, waxes, and oils are often used as conditioning agents. While such materials exert a very beneficial effect on hair, they also tend to promote greasy hair, or form a tacky surface on the hair which attracts dust and other airborne particulates. This causes hair to appear dull and dirty, and may also cause the hair to look flat with no body or fullness.

The use of alpha hydroxy acids (AHAs) in hair care products is known. However, AHAs in general are water soluble, thus they tend to be rinsed off the hair with water and do not remain on the hair to provide a significant, substantive conditioning effect to hair. On the other hand, fatty alcohols do provide a substantive conditioning effect to hair, but may tend to cause the hair to become greasy, dull, and without body or fullness.

It has most unexpectedly been discovered that hair care compositions containing alpha and/or beta hydroxy acid esters provide a good substantive conditioning effect to hair, improve shine, body, combing, and fullness, and at the same time do not cause hair to become greasy or tacky.

SUMMARY OF THE INVENTION

The invention is directed to a hair care composition comprising, by weight of the total composition:

0.1–20% cationic conditioning agent, 0.1–20% of one or more alpha or beta hydroxy acid esters, 0.1–30% fatty alcohol, 0.001–10% nonionic surfactant, and 5–95% water.

The composition are in the form of an after shampoo conditioner which is a water-in-oil or oil-in-water emulsion, preferably the latter.

DETAILED DESCRIPTION

All percentages mentioned herein are percentages by weight unless otherwise stated.

Conditioning Agent

The composition of the invention comprises 0.1–20%, preferably 0.5–15%, more preferably 1–12% by weight of the total composition of a cationic conditioning agent.

Suitable cationic conditioning agents are cationic polymers, quaternary ammonium salts or the salts of fatty amines. Quaternary ammonium salts have the formula:

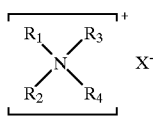

wherein $R_1$ is an aliphatic group of 1 to 22 carbon atoms, or aromatic, aryl, or alkaryl group having 12 to 22 carbon atoms; $R_2$ and $R_3$ are each independently an aliphatic group having 1–22 carbon atoms; and $R_4$ is an alkyl group of from 1 to 3 carbon atoms, and X is an anion selected from halogen, acetate, phosphate, nitrate and methyl sulfate radicals. The aliphatic groups may contain, in addition to carbon atoms, ether linkages as well as amido groups. Suitable quaternary ammonium compounds may be mono-long chain alkyl, di-long chain alkyl, tri-long chain alkyl, and the like. Examples of such quaternary ammonium salts include behenalkonium chloride, behentrimonium chloride, behentrimonium methosulfate, benzalkonium chloride, benzethonium chloride, benzyl triethyl ammonium chloride, cetalkonium chloride, cetrimonium chloride, cetrimonium bromide, cetrimonium methosulfate, cetrimonium tosylate, cetylpyridinium chloride, dibehenyl/diarachidyl dimonium chloride, dibehenyldimonium chloride, dibehenyldimonium methosulfate, dicapryl/dicaprylyl dimonium chloride, Other quaternary ammonium salts useful as the cationic conditioning agent are compounds of the general formula:

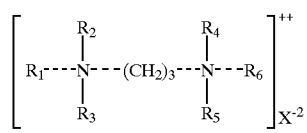

wherein $R_1$ is an aliphatic group having 16 to 22 carbon atoms, $R_2$, $R_3$, $R_4$, $R_5$, and $R_6$ are the same or different and are selected from alkyls having 1 to 4 carbon atoms and X is an anion as above defined.

Amides which exhibit the general formulas set forth below are also suitable conditioning agents:

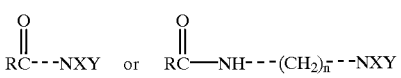

wherein R is a straight or branched chain saturated or unsaturated alkyl having 6 to 30 carbon atoms, n is an integer from 1 to 4, and X and Y are each independently H, or $C_{1-6}$ lower alkyl. Preferred is an amide of the formula:

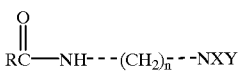

wherein R is a $C_{12-22}$ straight or branched chain alkyl, n is an integer from 1 to 4, and X is lower alkyl, preferably methyl.

Also suitable are amidoamine salts, which are the condensation products of fatty acids with a polyfunctional amines, for example, those having the formula $RCONH(CH_2)_nNR_1R_2$ where RCO is a fatty acyl group such as stearoyl, $R_1$ and $R_2$ are methyl or ethyl, and n is 2 or 3. Examples of such compounds include stearmidopropyl dimethylamine. Particularly preferred are amidoamine compounds complexed with a mild dimer acid, such as di(behenamidopropyl dimethyl amine) dimer dilinoleate or di(linoleamidopropyl dimethyl amine) dimer linoleate. Both ingredients are sold by Alzo, Inc. under the NECON tradename.

Also, quaternary imidazolinium salts having the following general formula are suitable as the cationic conditioning agent:

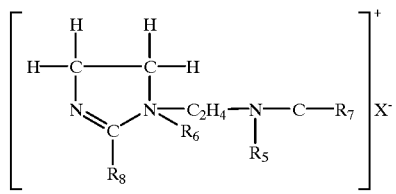

wherein $R_5$ is hydrogen or a $C_{1-4}$ alkyl; $R_6$ is a $C_{1-4}$ alkyl; $R_7$ is a $C_{8-22}$ alkyl; and $R_8$ is hydrogen, or a $C_{1-22}$ alkyl; and X is an anion as defined above.

Also suitable as the cationic hair conditioning agent are salts of fatty primary, secondary, or tertiary amines, wherein the substituted groups have 12 to 22 carbon atoms. Examples of such amines include dimethyl stearamine, dimethyl soyamine, stearylamine, myristylamine, tridecylamine, ethyl stearamine, and so on.

Also suitable as the cationic conditioning agent are cationic polymers such as:

(a) quaternary derivatives of cellulose ethers such as polymers sold under the tradename JR-125, JR-400, JR-30M.

(b) copolymers of vinylpyrrolidone having monomer units of the formula:

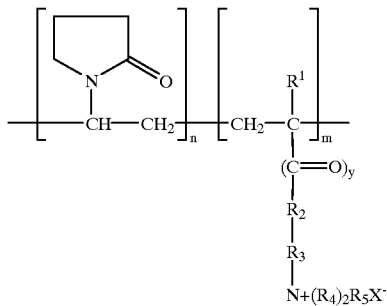

wherein $R^1$ is hydrogen or methyl, preferably methyl;
y is 0 or 1, preferably 1
$R^2$ is O or NH, preferably NH;
$R^3$ is $C_xH_{2x}$ where x is 2 to 18, or —$CH_2$—CHOH—$CH_2$—, preferably $C_xH_{2x}$ where x is 2;
$R^4$ is methyl, ethyl, phenyl, or $C_{1-4}$ substituted phenyl, preferably methyl; and
$R^5$ is methyl or ethyl, preferably methyl.

(c) Homopolymer of dimethyldiallylammonium chloride, or copolymer of dimethyldiallylammonium chloride and acrylamide. Such compounds are sold under the tradename MERQUAT by Merck.

(d) Homopolymers or copolymers derived from acrylic or methacrylic acid, selected from monomer units acrylamide, methylacrylamide, diacetone-acrylamide, acrylamide or methacrylamide substituted on the nitrogen by lower alkyl, alkyl esters of acrylic acid and methacrylic acid, vinylpyrrolidone, or vinyl esters.

(e) cationic silicones. As used herein, the term "cationic silicone" means any silicone polymer or oligomer having a silicon backbone, including polysiloxanes, having a positive charge on the silicone structure itself. Cationic silicones that may be used in the compositions of the invention include those corresponding to the following formula:

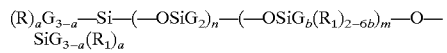

in which G is selected from the group consisting of H, phenyl, OH, $C_{1-10}$ alkyl, and is preferably $CH_3$; and a is 0 or an integer from 1 to 3, and is preferably 0; b is 0 or 1, preferably 1; the sum n+m is a number from 1 to 2,000 and is preferably 50 to 150; n is a number from 0 to 2000, and is preferably 50 to 150; and m is an integer from 1 to 2000, and is preferably 1 to 10; and $R_1$ is a monovalent radical of the formula $C_qH_{2q}L$ in which q is an integer from 2 to 8 and L is selected from the groups:

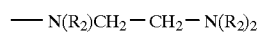
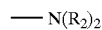
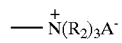
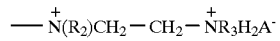

in which $R_2$ is selected from the group consisting of H, phenyl, benzyl, a saturated hydrocarbon radical, and is preferably an alkyl radical containing 1–20 carbon atoms; and A— is a halide ion.

(f) polymeric quaternary ammonium salts such as Polyquaternium 31, 33, 34, 35, 36, 37, and 39.

Also suitable are diquaternary polydimethylsiloxanes such as Quaternium-80, sold by Goldschmidt Corporation under the tradename ABIL-Quat 3272.

Examples of other cationic polymers that can be used in the compositions of the invention are disclosed in U.S. Pat. Nos. 5,240,450 and 5,573,709, which are hereby incorporated by reference.

The preferred compositions of the invention contain 0.5–15% by weight of a cationic conditioning agent which is selected from the group:

(a) quaternary ammonium salts have the formula:

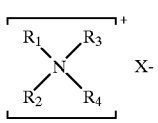

wherein $R_1$ is an aliphatic group of 1 to 22 carbon atoms, or aromatic, aryl, or alkaryl group having 12 to 22 carbon atoms; $R_2$ is an aliphatic group having 1–22 carbon atoms; $R_3$ and $R_4$ are each alkyl groups of from 1 to 3 carbon atoms, and X is an anion selected from halogen, acetate, phosphate, nitrate and methyl sulfate radicals;

(b) cationic silicones having the following formula:

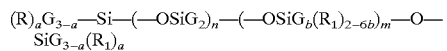

wherein G is H, phenyl, OH, $C_{1-10}$ alkyl; a is 0 or an integer from 1 to 3; b is 0 or 1; the sum n+m is a number from 1 to 2,000; n is a number from 0 to 2000; and m is an integer from 1 to 2000; and $R_1$ is a monovalent radical of the formula $C_qH_{2q}L$ in which q is an integer from 2 to 8 and L is selected from the groups:

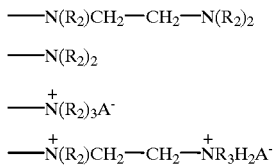

in which $R_2$ is H, phenyl, benzyl, a saturated hydrocarbon radical, and is preferably an alkyl radical containing 1–20 carbon atoms; and A— is a halide ion; and (c) an amide of the formula:

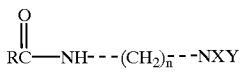

wherein R is a $C_{12-22}$ straight or branched chain alkyl, n is an integer from 1 to 4, and X is lower alkyl, preferably methyl, (d) an amidoamine salt, and mild dimer acids thereof Particularly preferred is where the cationic conditioning agent is selected from trimethylsilylamodimethicone, cetrimonium chloride, behentrimonium chloride, di(behenamidopropyl dimethyl amine) dimer dilinoleate, di(linoleamidopropyl dimethyl amine) dimer linoleate, or mixtures thereof.

Esters of Alpha or Beta Hydroxyacids

The hair care composition of the invention contains 0.001–20%, preferably 0.01–10%, more preferably 0.05–5% of a at least one alpha and/or beta hydroxy acid.

Esters of alpha hydroxy acids exhibit the following general formula:

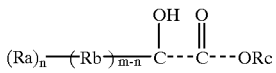

wherein Ra and Rb are each indendently H, F, Cl, I, Br, alkyl, aralkyl, or aryl group of saturated or unsaturated, isomeric or non-isomeric, straight or branched chain or cyclic form, having 1–30 carbon atoms; and in addition Ra and Rb may carry OH, CHO, COOH, or alkoxy groups having 1 to 10 carbon atoms; and Rc is a saturated or unsaturated straight or branched chain alkyl having 6 to 30 carbon atoms; and m and n are each independently integers from 0 to 2 with the proviso that n and m cannot both be zero.

Preferably Ra and Rb are each independently $C_{1-10}$ alkyl carrying OH, CHO, or COOH groups, or zero, with the proviso that n and m cannot both be zero, i.e. there is at least one Ra or Rb group; and Rc is a $C_{12-22}$ straight or branched chain saturated or unsaturated alkyl such as lauryl, myristyl, palmityl, stearyl, isostearyl, cetyl, linoleyl, oleyl, or linolenyl. Particularly preferred is wherein Ra is selected from $CH_2CHOHCOOH$, $CHOHCH_3$, and $CH_2OH$; and Rb is selected from 0 or $CH_2OH$; and Rc is a branched chain $C_{18}$ alkyl. Examples of such compounds are isostearyl lactate, isostearyl glycolate, isostearyl citrate, and mixtures thereof.

Also suitable are esters of beta hydroxy acids, formed by the reaction of a carboxylic acid having a beta hydroxy functionality, with an aliphatic alcohol, preferably an aliphatic alcohol having 6 to 30 carbons. Included within this group are beta hydroxy acids having the general formula:

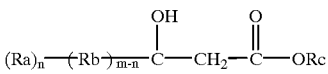

wherein Ra, Rb, Rc, and m and n are as defined above. Preferred is an ester of malic acid.

Most preferred is a mixture of alpha and beta hydroxy acid esters, in particular, a mixture of isostearyl malate, lactate, glycolate, and citrate. This material is sold by Alzo, Inc. under the tradename Dermol ALFA, which is a reaction product of a mixture of alpha and beta hydroxy acids derived from natural sources and isostearyl alcohol.

Fatty Alcohol

The composition of the invention contains 0.1–20%, preferably 0.5–10%, more preferably 1–8% of a fatty alcohol having the formula $RCH_2OH$ wherein R is a straight or branched chain saturated or unsaturated alkyl having at least about 6 to 30 carbon atoms. Examples of fatty alcohols suitable for use include behenyl alcohol, $C_{9-15}$ alcohols, caprylic alcohol, cetearyl alcohol, cetyl alcohol, coconut alcohol, decyl alcohol, lauryl alcohol, cetyl alcohol, myristyl alcohol, oleyl alcohol, palm alcohol, stearyl alcohol, tallow alcohol, and the like. The preferred compositions of the invention include a mixture of cetyl and stearyl alcohols.

Nonionic Surfactant

The compositions of the invention contain 0.001–10%, preferably 0.01–8%, more preferably 0.01–5% of a nonionic surfactant or emulsifier.

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms, and a straight or branched, saturated or unsaturated carbon chain. Examples of such ingredients include Beheneth 5–30, which is formed by the reaction of behenyl alcohol and ethylene oxide where the number of repeated ethylene oxide units is 5 to 30; Ceteareth 2–100, formed by the reaction of a mixture of cetyl and stearyl alcohol with ethylene oxide, where the number of repeating ethylene oxide units in the molecule is 2 to 100; Ceteth 1–45 which is formed by the reaction of cetyl alcohol and ethylene oxide, and the number of repeating ethylene oxide units is 1 to 45, and so on. Particularly preferred is Ceteareth 20, which is the reaction product of a mixture of cetyl and stearyl alcohol with ethylene oxide, and the number of repeating ethylene oxide units in the molecule is 20.

Also suitable as the nonionic surfactant are alkyoxylated carboxylic acids, which are formed by the reaction of a carboxylic acid with an alkylene oxide or with a polymeric ether. The resulting products have the general formula:

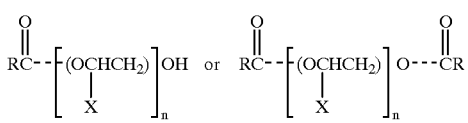

where RCO is the carboxylic ester radical, X is hydrogen or lower alkyl, and n is the number of polymerized alkoxy groups. In the case of the diesters, the two RCO— groups do not need to be identical. Preferably, R is a $C_{6-30}$ straight or branched chain, saturated or unsaturated alkyl, and n is from 1–100.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula;

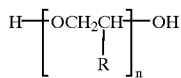

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20–85, sorbitan oleate, sorbitan palmitate, sorbitan sesquiisostearate, sorbitan stearate, and so on.

Also suitable as nonionic surfactants are silicone surfactants, which are defined as silicone polymers which have at least one hydrophilic radical and at least one lipophilic radical. The silicone surfactant used in the compositions of the invention are organosiloxane polymers that may be a liquid or solid at room temperature. The organosiloxane surfactant is generally a water-in-oil or oil-in-water type surfactant which is, and has an Hydrophile/Lipophile Balance (HLB) of 2 to 18. Preferably the organosiloxane is a nonionic surfactant having an HLB of 2 to 12, preferably 2 to 10, most preferably 4 to 6. The HLB of a nonionic surfactant is the balance between the hydrophilic and lipophilic portions of the surfactant and is calculated according to the following formula:

$$HLB = 7 + 11.7 \times \log M_W/M_O$$

where $M_W$ is the molecular weight of the hydrophilic group portion and $M_O$ is the molecular weight of the lipophilic group portion.

The term "organosiloxane polymer" means a polymer containing a polymeric backbone including repeating siloxy units that may have cylic, linear or branched repeating units, e.g. di(lower)alkylsiloxy units, preferably dimethylsiloxy units. The hydrophilic portion of the organosiloxane is generally achieved by substitution onto the polymeric backbone of a radical that confers hydrophilic properties to a portion of the molecule. The hydrophilic radical may be substituted on a terminus of the polymeric organosiloxane, or on any one or more repeating units of the polymer. In general, the repeating dimethylsiloxy units of modified polydimethylsiloxane emulsifiers are lipophilic in nature due to the methyl groups, and confer lipophilicity to the molecule. In addition, longer chain alkyl radicals, hydroxypolypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the organosiloxane polymer in accordance with the invention should have at least one hydrophilic portion and one lipophilic portion.

The term "hydrophilic radical" means a radical that, when substituted onto the organosiloxane polymer backbone, confers hydrophilic properties to the substituted portion of the polymer. Examples of radicals that will confer hydrophilicity are hydroxy-polyethyleneoxy, hydroxyl, carboxylates, and mixtures thereof.

The term "lipophilic radical" means an organic radical that, when substituted onto the organosiloxane polymer backbone, confers lipophilic properties to the substituted portion of the polymer. Examples of organic radicals which will conver lipophilicity are $C_{1-40}$ straight or branched chain alkyl, fluoro, aryl, aryloxy, $C_{1-40}$ hydrocarbyl acyl, hydroxypolypropyleneoxy, or mixtures thereof. The $C_{1-40}$ alkyl may be non-interrupted, or interruped by one or more oxygen atoms, a benzene ring, amides, esters, or other functional groups.

The polymeric organosiloxane surfactant used in the invention may have any of the following general formulas:

$$M_xQ_y, \text{ or}$$

$$M_xT_y, \text{ or}$$

$$MD_xD'_yD''_zM$$

wherein each M is independently a substituted or unsubstituted trimethylsiloxy endcap unit. If substituted, one or more of the hydrogens on the endcap methyl groups are substituted, or one or more methyl groups are substituted with a substituent that is a lipophilic radical, a hydrophilic radical, or mixtures thereof. T is a trifunctional siloxy unit having the empirical formula $RR'SiO_{1.5}$ or $RRSiO_{1.5}$. Q is a quadrifunctional siloxy unit having the empirical formula $SiO_2$, and D, D', D", x, y, and z are as set forth below, with the proviso that the compound contains at least one hydrophilic radical and at least one lipophilic radical. Preferred is a linear silicone of the formula:

$$MD_xD'_yD''_zM$$

wherein $M = RRRSiO_{1/2}$

D and $D' = RR''SiO_{2/2}$ $D'' = RRSiO_{2/2}$ x, y, and z are each independently 0–1000, where R is methyl or hydrogen, and R' is a hydrophilic radical or a lipophilic radical, with the proviso that the compound contains at least one hydrophilic radical and at least one lipophilic radical.

Most preferred is wherein

M = trimethylsiloxy $D = Si[(CH_3)][(CH_2)_nCH_3]O_{2/2}$ where n=0–40, $D' = Si[(CH_3)][(CH_2)_o—O—PE)]O_{2/2}$ where PE is $(—C_2H_4O)_a(—C_3H_6O)_bH$, o×0–40, a=1–100 and b=1–100, and $D'' = Si(CH_3)_2O_{2/2}$ More specifically, suitable silicone surfactants have the formula:

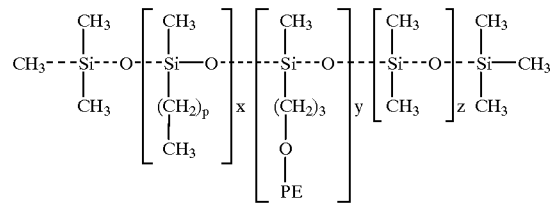

wherein p is 0–40, preferably 12–20, most preferably 15, and

PE is $(—C_2H_4O)_a(—C_3H_6O)_b—H$ where x, y, z, a, and b are such that the maximum molecular weight of the polymer is approximately 50,000.

Another type of preferred organosiloxane emulsifier suitable for use in the compositions of the invention are emulsifiers sold by Union Carbide under the Silwet™ trademark. These emulsifiers are represented by the following generic formulas:

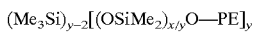

wherein PE=—$(EO)_m(PO)_nR$

R=lower alkyl or hydrogen
Me=methyl
EO is polyethyleneoxy
PO is polypropyleneoxy
m and n are each independently 1–5000
x and y are each independently 0–5000, and

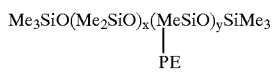

wherein PE=—$CH_2CH_2CH_2O(EO)_m(PO)_nZ$

Z=lower alkyl or hydrogen, and
Me, m, n, x, y, EO and PO are as described above, with the proviso that the molecule contains a lipophilic portion and a hydrophilic portion. Again, the lipophilic portion can be supplied by a sufficient number of methyl groups on the polymer Also suitable as nonionic silicone surfactants are hydroxy-substituted silicones such as dimethiconol, which is defined as a dimethyl silicone substituted with terminal hydroxy groups.

Examples of silicone surfactants are those sold by Dow Coming under the tradename Dow Coming 3225C Formulation Aid, Dow Coming 190 Surfactant, Dow Coming 193 Surfactant, Dow Coming Q2-5200, and the like are also suitable. In addition, surfactants sold under the tradename Silwet by Union Carbide, and surfactants sold by Troy Corporation under the Troysol tradename, those sold by Taiwan Surfactant Co. under the tradename Ablusoft, those sold by Hoechst under the tradename Arkophob, are also suitable for use in the invention.

In the preferred compositions of the invention, the nonionic surfactant is an alkoxylated alcohol, or ether, formed by the reaction of a fatty alcohol with ethylene oxide; either alone or in combination with a hydroxy-substituted dimethicone. Particularly preferred is Ceteareth-20, which is the reaction product of a mixture of cetyl and stearyl alcohol with ethylene oxide, and the number of repeating ethylene oxide units in the molecule is 20 and dimethiconol.

Particularly preferred is a nonionic silicone referred to as trimethylsilylamodimethicone, having the following formula:

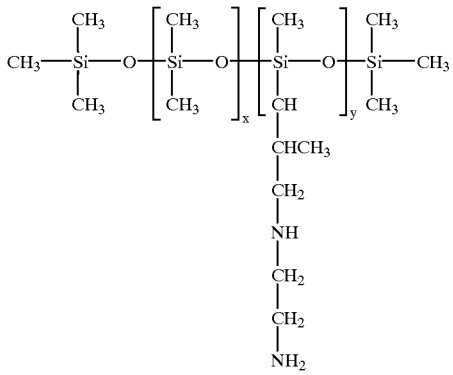

wherein x and y are 1–100,000.

Other Ingredients

It may be desired to add other ingredients to the conditioner compositions to enhance the effects and provide other benefits. A variety of such materials may be used.

Silicones

It may also be desireable to include silicones in the hair conditioning compositions of the invention. Such silicones are known to improve wet and dry combability of hair, exert conditioning effects, and enhance shine and manageability. Suggested ranges of silicone are 0.01–20%, preferably 0.05–15%, more preferably 0.1–10% by weight of the total composition.

Suitable silicones include linear and cyclic volatile polydimethylsiloxanes, and linear nonvolatile polydimethylsiloxanes, organosiloxane surfactants, and silicone resins.

Volatile silicones are linear or cyclic silicones having a measureable vapor pressure, which is defined as a vapor pressure of at least 2 mm. of mercury at 20° C. Examples of volatile silicones are cyclic silicones having the general formula:

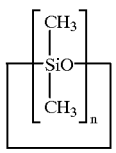

where n=3–7.

Also, linear volatile silicones that may be used in the compositions of the invention have the general formula:

where n=0–7, preferably 0–5.

The silicone may comprise water insoluble nonvolatile silicone fluids including polyalkyl siloxanes, polyaryl siloxanes, polyalkylaryl siloxane copolymers, and mixtures thereof. Such silicones have the following general formula:

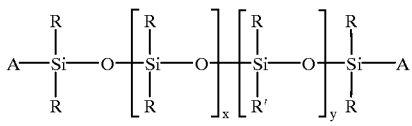

wherein R and R' are each independently alkyl, or aryl, and x and y are each independently 0–100,000 with the proviso that there is at least one of either x or y, and A is siloxy endcap unit. Preferred is where A is methyl, and R and R' are methyl.

Silicone resins are also suitable for use in the compositions of the invention. Silicone resins are siloxy silicate polymers having the following general formula:

wherein R, R' and R" are each independently a $C_{1-10}$ straight or branched chain alkyl or phenyl, and x and y are such that the ratio of $(RR'R'')_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 2-0749 and 2-0747, which is a blend of about 40–60% volatile silicone and 40–60% trimethylsiloxy silicate. Dow Corning 2-0749 in particular, is a fluid containing about 50% trimethylsiloxy silicate and about 50% cyclomethicone. The fluid has a viscosity of 200–700 centipoise at 25° C., a specific gravity of 1.00 to 1.10 at 25° C., and a refractive index of 1.40–1.41.

Also suitable are silicone graft or block copolymers such as vinyl silicone copolymers having the general formula:

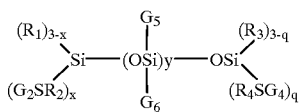

wherein $G_5$ is a monovalent moiety which can independently be the same of different selected from the group consisting of alkyl, aryl, alkaryl, alkoxy, alkylamino, fluoroalkyl, hydrogen, and —ZSA; where A is a vinyl polymeric segment consisting essential of a polymerized free radically polymerizable monomer, and Z is a divalent linking group. Useful divalent linking groups Z include C1–10 alkylene, alkylarylene, arylene, and alkoxyalkylene. Preferably Z is methylene or propylene; and wherein G6 is a monovalent moiety which can independently be the same or different, and is alkyl, aryl, alkaryl, alkoxy, alkylamino, fluoroalkyl, hydrogen, and —ZSA; and wherein $G_2$ is A; and $G_4$ is A; and $R_1$ is a monovalent moiety which is independently the same or different, and is selected from alkyl, aryl, alkaryl, alkoxy, alkylamino, fluoroalkyl, hydrogen, and hydroxyl. Preferably $R_1$ is a monovalent moiety which is C1–4 alkyl and hydroxyl, most preferably methyl. $R_2$ can be independently the same or different, and is a divalent linking group such as $C_{1-10}$ alkylene, arylene, alkarylene, and alkoxyalkylene. $R_3$ is a monovalent moiety which can independently be the same or different and is alkyl, aryl, alkaryl, alkoxy, alkylamino, fluoroalkyl, hydrogen, or hydroxyl. $R_4$ can independently be the same or different and are divalent linking groups including $C_{1-10}$ alkylene, arylene, alkarylene, and alkoxyalkylene. The designation x is an integer of 0–3, y is an integer of 5 or greater, and q is an integer of 0–3. Such vinyl silicone graft or block copolymers are disclosed in U.S. Pat. No. 5,468,477, which is hereby incorporated by reference. Preferred is a vinyl silicone copolymer sold by 3-M Company under the tradename VS-80, which also has the CTFA name Polysilicone-8 and the chemical name poly(dimethylsiloxane)-g-polyacrylates. Polysilicone 8 is soluble in water and miscible with most organic solvents, a colorless to slightly yellow liquid having a specific gravity of 1.013 at 25° C., a viscosity of about 20 centipoise at 25° C., and the polymer has a molecular weight of about 26,000.

Also suitable for use as silicone graft or block copolymers are acryl-silicone graft copolymers as disclosed in U.S. Pat. No. 5,061,481, which is hereby incorporated by reference. These acryl-silicone copolymers may be prepared by the radical polymerization of a dimethylpolysiloxane compound having a polymerizable radical group on one of the molecular chain terminals, and a radically polymerizable monomer comprising predominantly an acrylate or methacrylate or both. The dimethylpolysiloxane having a polymerizable radical group on one of the molecular chain terminals is represented by the following general formula:

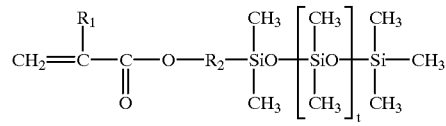

wherein $R_1$ is methyl or hydrogen, $R_2$ is a divalent linear or branched hydrocarbon group having 1–10 carbon atoms and optionally containing one or two ether bonds therein, and 1 is 3–300. Examples of $R_2$ include —$CH_2$—, —$(CH_2)_3$—, —$(CH_2)_5$—, —$(CH_2)_8$—, —$(CH_2)_{10}$—, —$CH_2$—CH($CH_3$)—$CH_2$—, and so on.

Also suitable as a silicone graft or block copolymers are those having a vinyl, methacrylic, or acrylic backbone and pendant siloxane groups and pendant fluorochemical groups. Such polymers preferably comprise comprise repeating A, C, D and optionally B monomers wherein:

A is at least one free radically polymerizable acrylic or methacrylic ester of a 1,1,-dihydroperfluoroalkanol or analog thereof, omega-hydridofluoroalkanols, fluoroalkylsulfonamido alcohols, cyclic fluoroalkyl alcohols, and fluoroether alcohols, B is at least one reinforcing monomer copolymerizable with A, C is a monomer having the general formula $X(Y)_nSi(R)_{3-m}Z_m$ wherein X is a vinyl group copolymerizable with the A and B monomers, Y is a divalent linking group which is alkylene, arylene, alkarylene, and aralkylene of 1 to 30 carbon atoms which may incorporate ester, amide, urethane, or urea groups, n is zero or 1;

m is an integer of from 1 to 3,

R is hydrogen, $C_{1-4}$ alkyl, aryl, or alkoxy,

Z is a monovalent siloxane polymeric moiety; and
D is at least one free radically polymerizable acrylate or methacrylate copolymer, Such polymers and their manufacture are disclosed in U.S. Pat. Nos. 5,209,924 and 4,972,037, which are hereby incorporated by reference.

Preferred is wherein the polymer is a combination of A, C, and D monomers wherein A is a polymerizable acrylic or methacrylic ester of a fluoroalkylsulfonamido alcohol, and where D is a methacrylic acid ester of a $C_{1-12}$ straight or branched chain alcohol, and C is as defined above. Most preferred is a polymer having moieties of the general formula:

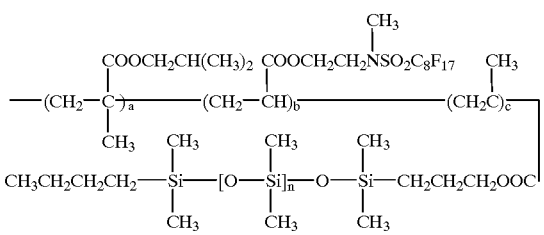

wherein a, b, and c are 1–100,000, and the terminal groups can be $C_{1-20}$ straight or branched chain alkyl, aryl, alkoxy, and the like. These polymers may be purchased from Minnesota Mining and Manufacturing Company under the tradenames "Silicone Plus" polymers. Most preferred is poly (isobutyl methacrylate-co-methyl FOSEA)-g-poly (dimethylsiloxane) which is sold under the tradename SA 70-5 IBMMF.

The preferred compositions of the invention contain 0.1–10% of a silicone selected from cyclic volatile silicones, linear water insoluble nonvolatile silicones, and vinyl silicone copolymers, or mixtures thereof.

Oily Conditioning Agents

The compositions of the invention may additionally contain 0.05–10%, preferably 0.1–8%, more preferably 1–7% of an oily conditioning agent which is an organic, nonvolatile oil. The term "nonvolatile" means that the oil does not have a measureable vapor pressure, i.e. has a vapor pressure of less than about 2 mm. mercury at 20° C. Preferably, the nonvolatile oil has a viscosity ranging from 10 to 1,000,000 centipoise at 25° C., preferably 20 to 600,000 centipoise at 25° C.

The oil may comprise esters of the formula RCO—OR' wherein R and R' are each independently a $C_{1-25}$, preferably a $C_{4-20}$ straight or branched chain alkyl, alkenyl or alkoxycarbonylalkyl or alkylcarbonyloxyalkyl. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, and fatty alcohols such as oleyl alcohol, isocetyl alcohol, and the like, as well as the esters disclosed on pages 24–26 of the *C.T.F.A. Cosmetic Ingredient Handbook*, First Edition, 1988, which is hereby incorporated by reference.

The oil may also comprise glyceryl esters of fatty acids, or triglycerides, such as castor oil, lanolin oil, triisocetyl citrate, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

Also suitable as the oil are glyceryl esters (excluding fats and oils which are glyceryl esters of fatty acids) which are primarily fatty acid mono-di- and triglycerides which are modified by reaction with other alcohols, for example, acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and so on.

Also suitable as the oil are nonvolatile hydrocarbons such as isoparaffins, hydrogenated polyisobutene, mineral oil, squalene, petrolatum, and so on.

Also suitable as the oil are various lanolin derivatives such as acetylated lanolin, acetylated lanolin alcohol, and so on.

Also suitable as the oil are various fluorinated oils are fluoro guerbet esters or perfluropolyethers. Suitable perfluoropolyethers are disclosed in U.S. Pat. Nos. 5,183,589, 4,803,067, 5,183,588 all of which are hereby incorporated by reference. These perfluoropolyethers are commercially available from Montefluos under the trademark Fomblin.

Other suitable oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on.

Preferred nonvolatile oils are guerbet esters. The term "guerbet ester" means an ester which is formed by the reaction of a guerbet alcohol having the general formula:

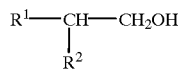

with a carboxylic acid having the general formula:

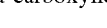

wherein $R^1$ and $R^2$ are each independently a $C_{4-20}$ alkyl and $R^3$ is a substituted or unsubstituted $C_{1-50}$ straight or branched chain saturated alkyl or alkylene, or phenyl, wherein the substituents are halogen, hydroxyl, carboxyl, and alkylcarbonylhydroxy. Preferably, the guerbet ester is a fluoro-guerbet ester which is formed by the reaction of a guerbet alcohol and carboxylic acid (as defined above), and a fluoroalcohol having the following general formula:

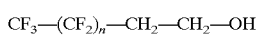

wherein n is from 3 to 40.

Examples of guerbet esters are as set forth in U.S. Pat. No. 5,488,121 which is hereby incorporated by reference. Suitable fluoro-guerbet esters are set forth in U.S. Pat. No. 5,312,968 which is hereby incorporated by reference. Most preferred are fluoro-substituted guerbet esters having the tentative CTFA name fluoro-octyldodecyl meadowfoamate. This ester is sold by Siltech, Norcross Georgia as Developmental Ester L61125A, under the tradename Silube GME-F; or a cyclic fluoro-guerbet ester sold under the tradename Fluorosil™ by Biosil, and having the chemical name dioctyldodecyl fluoroheptyl citrate.

In addition, the composition may contain 0.001–5%, preferably 0.005–4%, more preferably 0.01–3% by weight of humectant. The humectant is a hygroscopic ingredient that acts to moisturize the hair by attracting water. Suitable humectants are polyhydric and dihydric alcohols such as propylene glycol, glucose, fructose, glycerin, maltitol, and so on. Preferred is wherein the conditioning composition of the invention contains 0.01–3% of a dihydric alcohol, in particular, propylene glycol.

The invention will be further described in connection with the following examples which are set forth for the purpose of illustration only.

EXAMPLE 1
A hair conditioner composition was made according to the following formula:

| | w/w % |
|---|---|
| Water | QS |
| Citric acid | 0.15 |
| Methyl paraben | 0.20 |
| Propyl paraben | 0.05 |
| Panthenol | 0.01 |
| Cetearyl alcohol | 2.00 |
| Stearyl alcohol | 1.20 |
| Cetyl alcohol | 2.00 |
| Propylene glycol | 2.00 |
| Ceteareth-20 | 0.50 |
| Trimethylsilylamodimethicone | 1.00 |
| Fragrance | 0.50 |
| Pantethine | 0.001 |
| Behentrimonium chloride | 2.70 |
| Dimethicone/dimethiconol | 0.30 |
| Dilinoleamidopropyl dimethylamine dimer linoleate | 1.40 |
| Propylene glycol dicaprylate/dicaprate//PPG1-trideceth-6* | 2.0 |
| Octyldodecyl fluoroheptyl citrate and cyclomethicone (40%) | 1.0 |
| Isostearyl malate/lactate/glycolate/citrate** | 0.30 |

*Polyquaternium 37
**Dermol ALFA, Alzo Inc.

The above composition was made by mixing the ingredients in water and stirring well.

EXAMPLE 2
A hair conditioner composition was made according to the following formula:

| | w/w % |
|---|---|
| Fragrance | 0.80 |
| Kathon CG (preservative) | 0.04 |
| Hydroxyethylcellulose | 0.50 |
| Cetyl alcohol | 1.20 |
| Stearamidopropyldimethylamine | 0.50 |
| Cetearyl alcohol/ceteareth-20 | 2.0 |
| Stearyl alcohol | 1.0 |
| Propylene glycol | 2.0 |
| Di(behenamidopropyl dimethyl amine)dimer linoleate | 1.3 |
| Methyl paraben | 0.2 |
| Behentrimonium chloride | 2.9 |
| Propyl paraben | 0.025 |
| Citric acid | 0.20 |
| Polysilicone-8* | 0.50 |
| Trimethylsilylamodimethicone/octoxynol 40 isolaureth-6/propylene glycol | 2.0 |
| Sphingolipids | 0.10 |
| Isostearyl cjtrate/glycolate/lactate/malate** | 0.30 |
| Dioctyldodecyl fluoroheptyl citrate in cyclomethicone (40%) | 1.00 |

*Poly(dimethylsiloxane)-g-acrylates, sold by 3-M Company under the tradename VS-80.
**Dermol ALFA, sold by Alzo, Inc.

EXAMPLE 3
A hair conditioner composition was made according to the following formula:

| | w/w % |
|---|---|
| Water | QS |
| Citric Acid | 0.15 |
| Methyl paraben | 0.20 |
| Propyl paraben | 0.05 |
| Panthenol | 0.01 |
| Cetearyl alcohol | 2.00 |
| Stearyl alcohol | 1.20 |
| Cetyl alcohol | 1.00 |
| Ceteareth-20 | 0.50 |
| Trimethylsilylamodimethicone/tallow trimonium chloride/nonoxynol-10 | 2.00 |
| Fragrance | 0.50 |
| Behentrimonium chloride | 2.00 |
| Dilinoleamidopropyl dimethylamine dimer linoleate | 1.25 |
| Isostearyl malate/lactate/glycolate/citrate* | 0.30 |
| Stearamidopropyl dimethyl amine | 0.75 |
| Hydroxyethylcellulose | 0.75 |
| Cocamidopropyl betaine | 2.00 |
| Kathon CG | 0.04 |
| Dimethicone copolyol eicosanate | 0.01 |

*Dermol ALFA, Alzo, Inc.

The above composition was made by mixing the ingredients in water and stirring well.

While the invention has been described in connection with the preferred embodiment, it is not intended to limit the scope of the invention to the particular form set forth, but, on the contrary, it is intended to cover such alatematives, modifications, and equivalents as may be included within the spirit and scope of the invention as defined by the appended claims.

We claim:

1. A hair conditioner composition comprising, by weight of the total composition:

0.1–20% of a cationic conditioning agent selected from the group consisting of:
   (a) a quaternary ammonium salt having the formula:

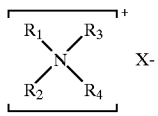

wherein $R_1$ is an aliphatic group of 1 to 22 carbon atoms, or aromatic, aryl, or alkaryl group having 12 to 22 carbon atoms; $R_2$ and and $R_3$ are each independently an aliphatic group having 1–22 carbon atoms; and $R_4$ is an alkyl group of from 1 to 3 carbon atoms, and X is an anion selected from halogen, acetate, phosphate, nitrate and methyl sulfate radicals.

(b) a cationic silicone having the following formula:

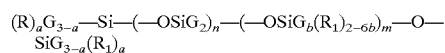

wherein G is H, phenyl, OH, $C_{1-10}$ alkyl; a is 0 or an integer from 1 to 3; b is 0 or 1; the sum n+m is a number from 1 to 2,000; n is a number from 0 to 2000; and m is an integer from 1 to 2000;

and $R_1$ is a monovalent radical of the formula $C_qH_{2q}L$ in which q is an integer from 2 to 8 and L is selected from the groups:

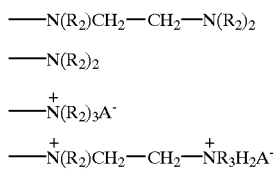

in which $R_2$ is H, phenyl, benzyl, or an alkyl radical containing 1–20 carbon atoms; and A— is a halide ion;

(c) an amide of the formula:

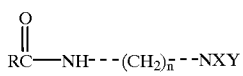

wherein R is a $C_{12-22}$ straight or branched chain alkyl, n is an integer from 1 to 4, and X is H or $C_{1-6}$alkyl, (c) an amidoamine salt; and
(d) mixtures thereof;

0.1–20% of a mixture of isostearyl citrate, isostearyl lactate, isostearyl malate, and isostearyl glycolate, 0.1–30% fatty alcohol having the formula ROH wherein R is a straight or branched chain alkyl having 6 to 30 carbon atoms, 0.001–10% nonionic surfactant, and 5–95% water.

2. The composition of claim 1 wherein the quaternary ammonium salt, $R_1$ is a $C_{12-22}$ alkyl and $R_2$, $R_3$, and $R_4$ are methyl.

3. The composition of claim 2 wherein the quaternary ammonium salt is benehtrimonium chloride, cetrimonium chloride, or mixtures thereof.

4. The composition of claim 1 wherein the amide is di(behenamidopropyl dimethyl amine) dimer dilinoeate, di(linoleamidopropyl dimethyl amine) dimer linoleate, or mixtures thereof.

5. The composition of claim 1 wherein the fatty alcohol is selected from the group consisting of cetyl alcohol, stearyl, alcohol, and mixtures thereof.

6. The composition of claim 1 wherein the nonionic surfactant is an alkoxylated alcohols formed by the reaction of an alcohol with an alkylene oxide.

7. The composition of claim 6 wherein the alkoxylated alcohol is formed by the reaction of ethylene oxide and a fatty alcohol having 6 to 30 carbon atoms.

8. The composition of claim 6 wherein the nonionic surfactant is formed by the reaction of ethylene oxide and a mixture of cetyl and stearyl alcohol.

9. The composition of claim 8 wherein the nonionic surfactant is Ceteareth-20.

10. The composition of claim 1 additionally comprising 0.01–20% of a silicone conditioning agent.

11. The composition of claim 10 wherein the silicone conditioning agent is selected from the group consisting of:

(a) cyclic volatile silicones having the general formula:

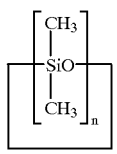

where n=3–7;

(b) linear volatile silicones having the general formula:

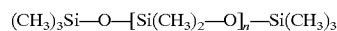

where n=0–7

(c) water insoluble nonvolatile silicone fluids having the general formula:

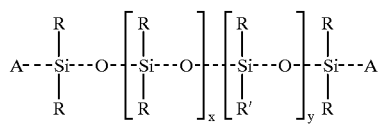

wherein R and R' are each independently alkyl, or aryl, and x and y are each independently 0–100,000 with the proviso that both x and y cannot be zero, and A is siloxy endcap unit.

(d) trialkylsiloxysilicate polymers having the general formula:

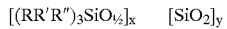

wherein R, R' and R" are each independently a $C_{1-10}$ straight or branched chain alkyl or phenyl, and x and y are such that the ratio of $(RR'R")_3SiO_{1/2}$ units to $SiO_2$ units is 0.5 to 1 to 1.5 to 1

(e) vinyl silicone copolymers having the general formula:

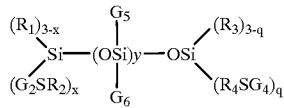

wherein:

$G_5$ is a monovalent moiety which can independently be the same of different selected from the group consisting of alkyl, aryl, alkaryl, alkoxy, alkylamino, fluoroalkyl, hydrogen, and —ZSA;

A is a vinyl polymeric segment consisting essentially of a polymerized free radically polymerizable monomer, Z is a divalent linking group which is $C_{1-10}$ alkylene, alkylarylene, arylene, and alkoxyalkylene, $G_6$ is a monovalent moiety which can independently be the same or different, and is alkyl, aryl, alkaryl, alkoxy, alkylamino, fluoroalkyl, hydrogen, and —ZSA, $G_2$ is A, $G_4$ is A, $R_1$ is a monovalent moiety which is independently the same or different, and is selected from alkyl, aryl, alkaryl, alkoxy, alkylamino, fluoroalkyl, hydrogen, and hydroxyl, $R_2$ can be independently the same or different, and is a divalent linking group which is $C_{1-10}$ alkylene, arylene, alkarylene, and alkoxyalkylene, R₃ is a monovalent moiety which can independently be the same or different and is alkyl, aryl, alkaryl, alkoxy, alkylamino, fluoroalkyl, hydrogen, or hydroxyl, R₄ can independently be the same or different and are divalent linking groups selected from the group consisting of C$_{1-10}$ alkylene, arylene, alkarylene, and alkoxyalkylene, x is an integer of 0–3, y is an integer of 5 or greater, and q is an integer of 0–3.

(f) acryl-silicone graft copolymers prepared by the radical polymerization of a dimethylpolysiloxane compound having a polymerizable radical group on one of the molecular chain terminals, having the following general formula:

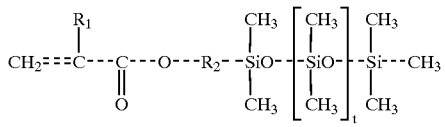

wherein R₁ is methyl or hydrogen, R₂ is a divalent linear or branched hydrocarbon group having 1–10 carbon atoms and optionally containing one or two ether bonds therein, and t is 3–300; with an acrylate or methacrylate or both; and (g) acryl-silicone copolymers having a methacrylic or acrylic backbone and pendant siloxane groups and pendant fluorochemical groups;

(h) hydroxy substituted polydimethylsiloxanes, and (i) mixtures thereof.

* * * * *